United States Patent
Delaney et al.

(10) Patent No.: US 7,738,628 B2
(45) Date of Patent: Jun. 15, 2010

(54) SHIELDED SAMPLE CELL INSERTION AND REMOVAL APPARATUS FOR X-RAY ANALYZER

(75) Inventors: Rory D. Delaney, Burnt Hills, NY (US); Brian W. Gallagher, Guilderland, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 0 days.

(21) Appl. No.: 12/326,160

(22) Filed: Dec. 2, 2008

(65) Prior Publication Data

US 2009/0141865 A1 Jun. 4, 2009

Related U.S. Application Data

(60) Provisional application No. 61/005,212, filed on Dec. 3, 2007.

(51) Int. Cl.
*G21K 1/04* (2006.01)
*H05G 1/00* (2006.01)

(52) U.S. Cl. .......................... 378/44; 378/79

(58) Field of Classification Search ................ 378/44, 378/79–80, 47
See application file for complete search history.

(56) References Cited

U.S. PATENT DOCUMENTS

2003/0048870 A1* 3/2003 Greenbank et al. ............ 378/68
2004/0028179 A1* 2/2004 Rosso et al. .................. 378/70

* cited by examiner

*Primary Examiner*—Hoon Song
(74) *Attorney, Agent, or Firm*—Jeffrey Klembczyk, Esq.; Kevin P. Radigan, Esq.; Heslin Rothenberg Farley & Mesiti P.C.

(57) ABSTRACT

A shielded sample cell insertion and removal apparatus for an x-ray analysis instrument, including a sample cell setting to hold a sample cell, an outer surface of which exposes the sample to an x-ray engine; and a shielded area positioned over the sample cell, to shield an area beyond the sample cell from x-rays transmitted from the x-ray engine. Upon moving the apparatus into and out of the instrument, the sample cell is moved into and out of an analysis position, while retaining shielding of areas beyond the sample cell from x-rays transmitted from the x-ray engine of the instrument.

15 Claims, 5 Drawing Sheets

SHIELDED SAMPLE CELL INSERTION AND REMOVAL APPARATUS FOR X-RAY ANALYZER

CROSS-REFERENCE TO RELATED PATENT APPLICATION

This application claims the benefit of United States provisional patent application Ser. No. 61/005,212, filed Dec. 3, 2007, which is hereby incorporated herein by reference in its entirety.

TECHNICAL FIELD

This invention relates in general to sample handling for sample analysis, and in particular to a precision insertion and removal device in the form of a drop/lockable cylinder to present a sample cell accurately to an x-ray analyzer where minimization of x-ray leakage and precise positioning are required.

BACKGROUND OF THE INVENTION

X-ray analysis of samples is a growing area of interest across many industries such as medical, pharmaceutical, and petroleum. U.S. Pat. Nos. 6,934,359 and 7,072,439, incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of liquid samples. As one particular example, these patents disclose techniques for the determination of the level of sulfur in petroleum fuels, and a commercialized analyzer (SINDIE) is now in widespread use for this measurement at petroleum refining, pipeline, and terminal facilities.

Sample handling is of critical importance in such systems, as is x-ray shielding. It is a general requirement of bench-top x-ray analysis systems to minimize x-ray exposure during sample loading and unloading. Traditionally, this is accomplished by interlock systems which mechanically and/or electrically control an x-ray blocking "shutter" mechanism over the x-ray source. An interlock system senses an operator opening the system to load/unload a sample, and automatically activates the shutter to completely block any x-rays from transmitting through the now-open sample door, toward an operator. Implementation of shutter mechanisms can be complex and costly, therefore, there is a need for a sample insertion and removal system which simplifies the x-ray interlock and/or shutter requirements.

Moreover, any sample insertion and removal technique must also present the sample to the x-ray measurement engine at a precise distance (along a z-axis as discussed below) for proper alignment to the requisite x-ray analysis spot. This z-axis alignment is critically important for x-ray optic enabled analyzers (such as those disclosed in the above-incorporated U.S. Patents and discussed further below) because of the sensitivity of the measurement to the focal spots of one or two separate optics in the x-ray excitation and/or detection paths.

What is required, therefore, is a sample insertion and removal apparatus, which minimizes x-ray leakage and simplifies x-ray shutter design, and which provides precise alignment of a sample to an x-ray analyzer engine, especially an x-ray optic-enabled analyzer engine.

SUMMARY OF THE INVENTION

The shortcomings of the prior art are overcome and additional advantages are provided by the present invention which in one aspect is a shielded sample cell insertion and removal apparatus for an x-ray analysis instrument, including a sample cell setting to hold a sample cell, an outer surface of which exposes the sample to an x-ray engine; and a shielded area positioned over the sample cell, to shield an area beyond the sample cell from x-rays transmitted from the x-ray engine. Upon moving the apparatus into and out of the instrument, the sample cell is moved into and out of an analysis position, while retaining shielding of areas beyond the sample cell from x-rays transmitted from the x-ray engine of the instrument.

Further additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

Figure 1:
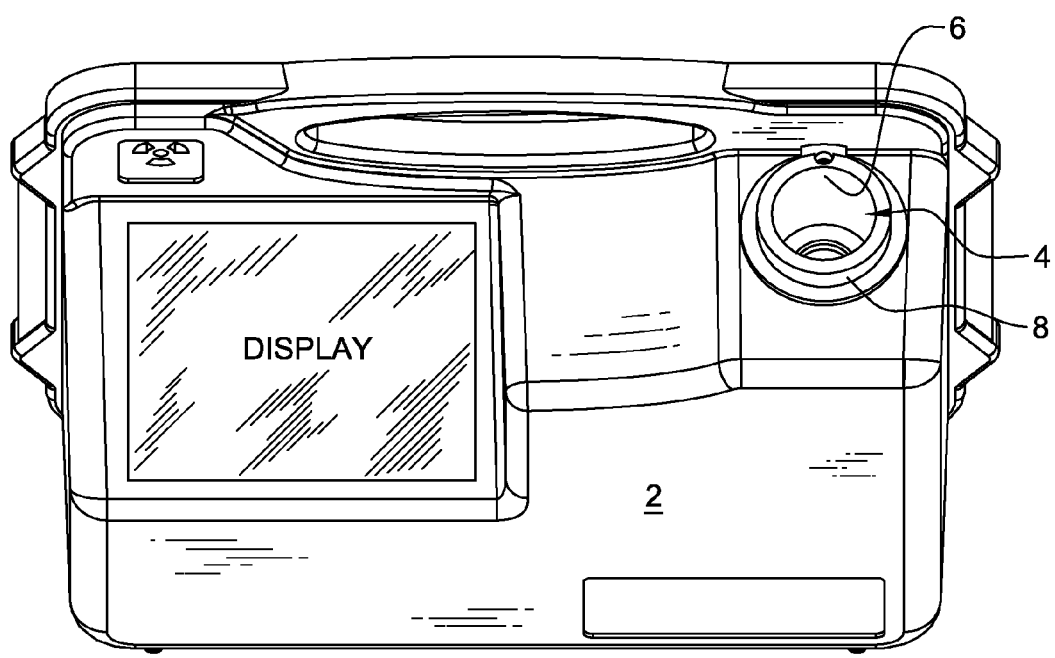
FIG. 1 is a perspective view of an x-ray analysis instrument requiring a shielded sample insertion and removal apparatus in accordance with one aspect of the present invention.

In accordance with the present invention, and with reference to FIG. 1, a mobile x-ray analyzer 2 includes an aperture 4 into which a sample handling apparatus is placed. Because of the potential of x-rays radiating from the analyzer 2 through aperture 4, the sample handling apparatus of the present invention includes the capability to precisely place a sample cell, and also a shielding capability.

Figure 2:
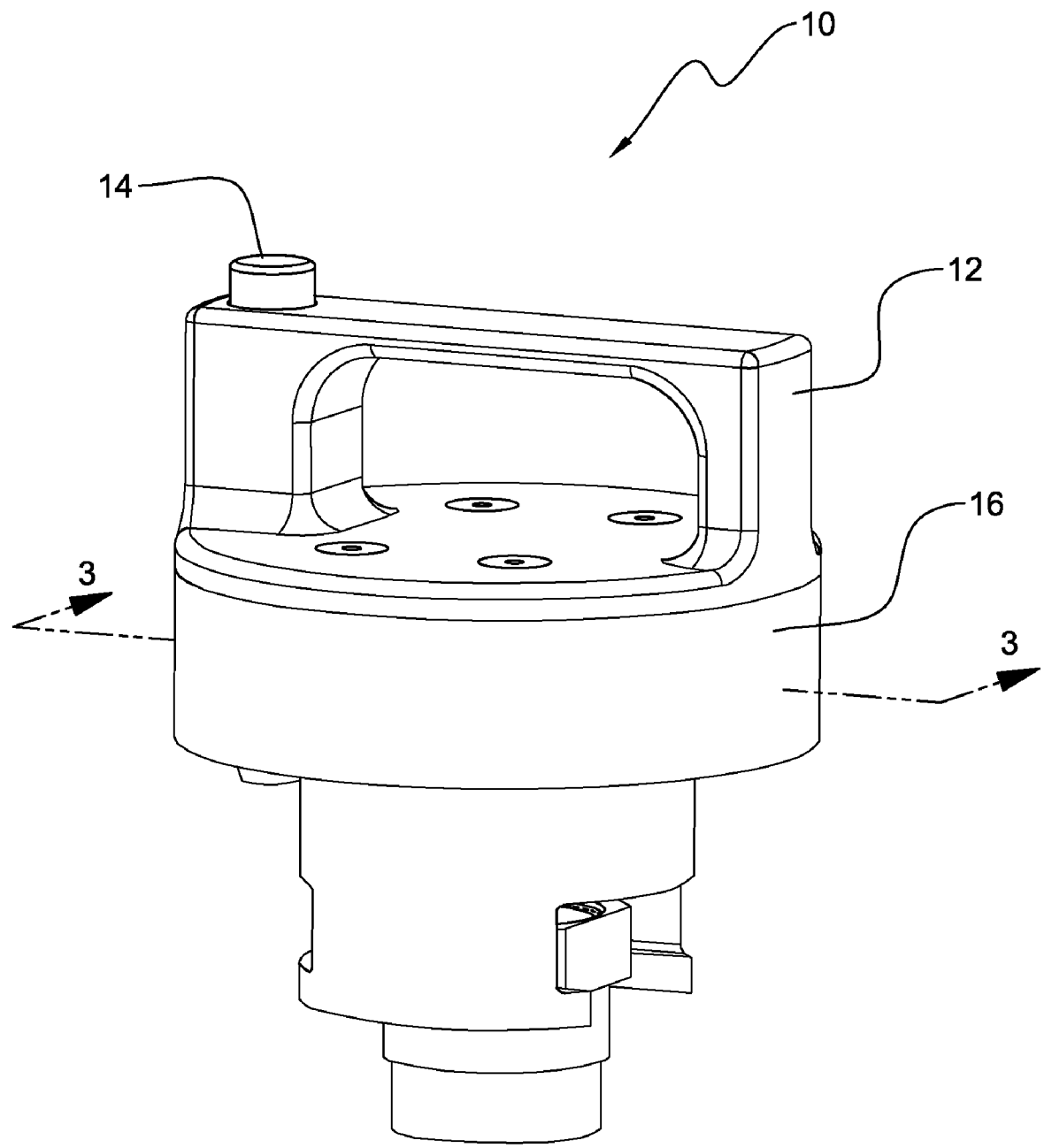
FIG. 2 is a perspective view of a shielded sample insertion and removal device in accordance with the present invention.

FIG. 2 is an isometric view of a sample insertion and removal apparatus 10 in accordance with the present invention. Apparatus 10 includes (generally oriented along a vertical axis) a handle 12 for ease of use, integrally formed within an outer body 16, an interior portion of which holds a sample cell as discussed further below. A push-pin locking assembly 14 locks/releases the apparatus from the analyzer.

Figure 3:
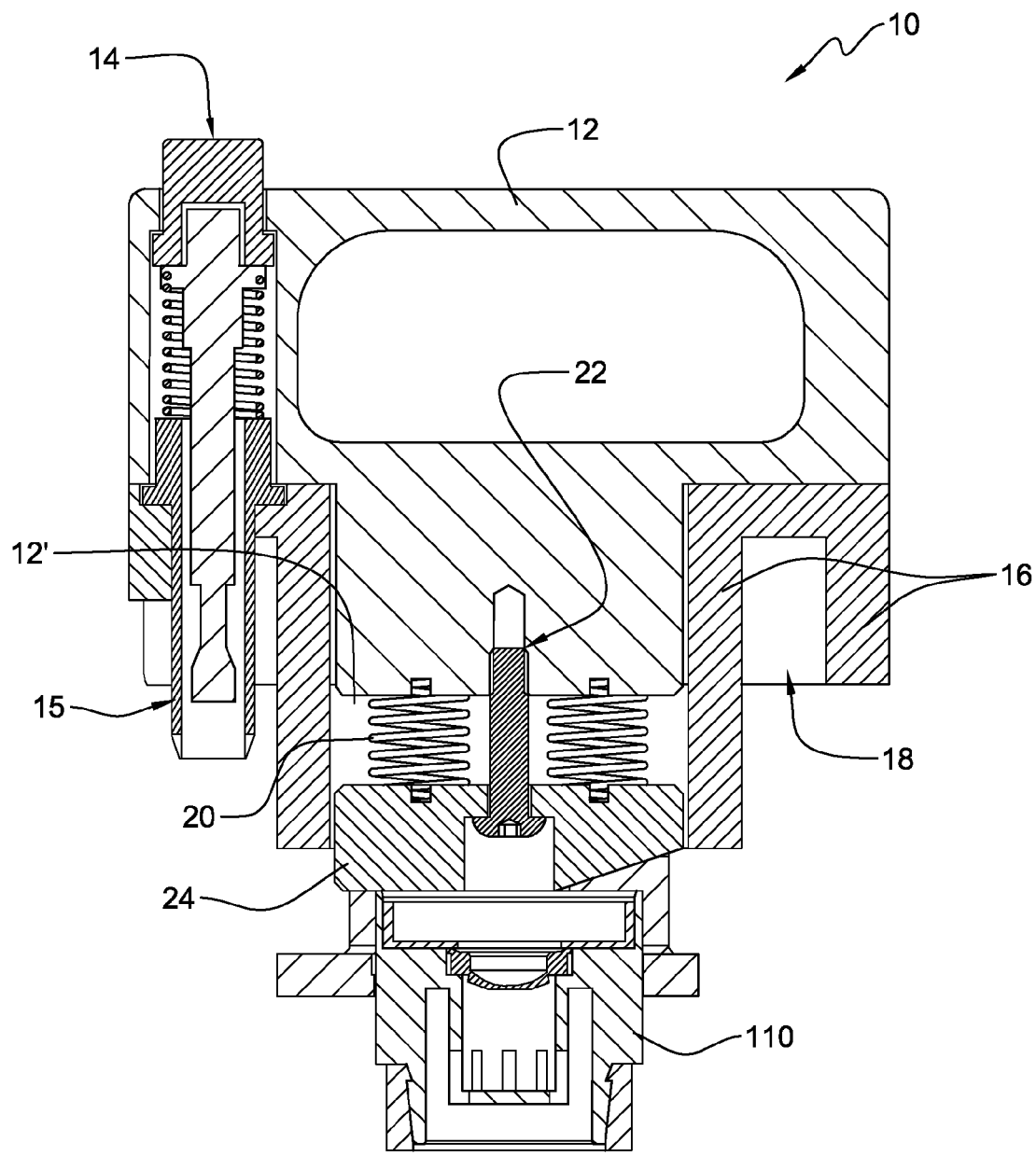
FIG. 3 is a sectional view of the apparatus of FIG. 2.
Figure 4:
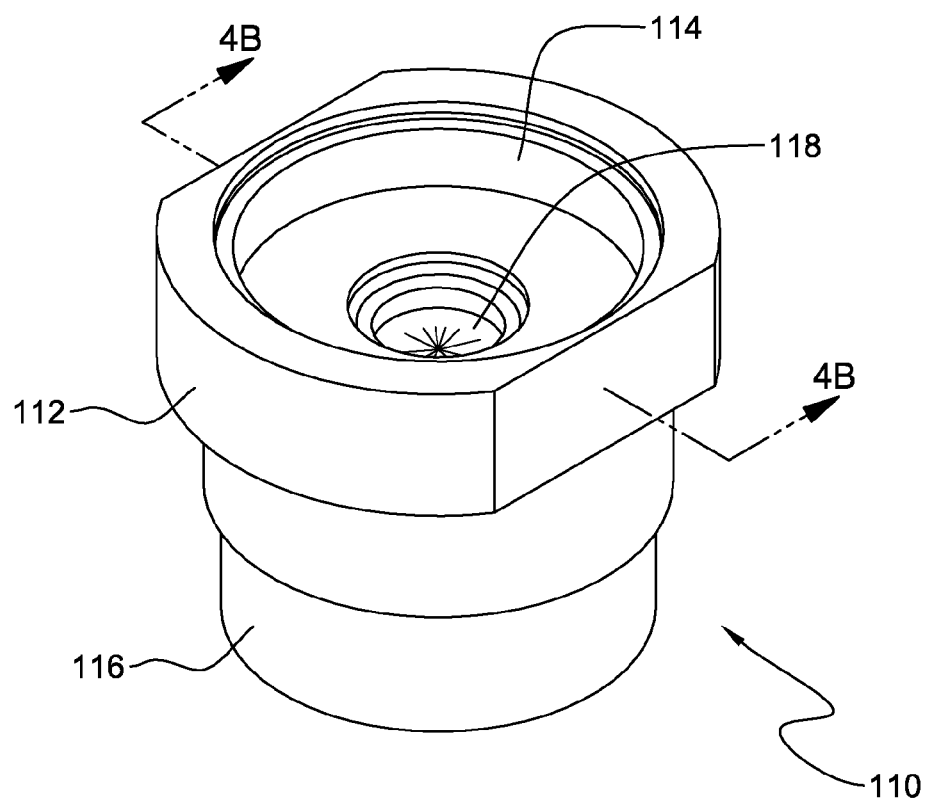
FIGS. 4-4a are an isometric and sectional view, respectively, of an exemplary sample cup useable in the present invention.

FIG. 3 is a sectional view of the apparatus 10 of FIG. 2. Here, sample cell 110 is positioned in a setting in a lower portion of apparatus 10. Sample cell can be slidably inserted into/removed from its setting which are formed of mating surfaces complimentary to those of sample cell 110. For example, horizontal edge 121 (FIG. 4b) can rest on a complimentary surface (not shown) of apparatus 10.

As discussed further below, sample cell 110 includes an x-ray transparent film upon which the cell is positioned when in its "analysis" position. This ensures proper z-axis alignment of the sample to an optic-enabled analysis engine. A vertically movable plate 24 ensures precise placement of cell 110 onto an analysis engine (not shown). Sample cell 110 is positioned under a movable plate 24, movably held within body 16. Plate 24 is engaged to compression springs 20 and axially guided by pin 22, which together ensure that cell 110 is placed over the x-ray engine with the requisite amount of gentle compression to ensure precise z-axis alignment (discussed further below with respect to FIG. 5).

Other features of the present invention include a push-pin locking assembly 14, having a lower portion 15 thereof, releasably operable by a button on the top end of the assembly. Push-pin assembly 14 descends into aperture 6 (FIG. 1) which is designed with complimentary locking grooves, etc, onto which ball bearings or other latchable means on the lower end of assembly 14 can engage. The assembly latches automatically when fully lowered into the aperture, thus locking the entire apparatus 10 into the analyzer; and can be released with the push of a button thereafter. Further alignment is provided by guide area 18, which can mate with complimentary, protruding edge 8 of analyzer 2.

When fully lowered over the x-ray engine, and locked into position, apparatus 10 provides an intrinsic x-ray shielding affect over the sample cell because of the mass of handle 12 and/or body 16. These components can be further designed with x-ray absorptive materials and/or plating (for example, on lower horizontal surfaces 12') to absorb and therefore block x-rays, which are upwardly transmitted into the lower end of sample cell 110. Also, any suitable trigger mechanisms can be used to open/close an x-ray shutter upon full insertion of the apparatus 10 into the analyzer, including simpler mechanical contact/trip switches.

Figure 4A:
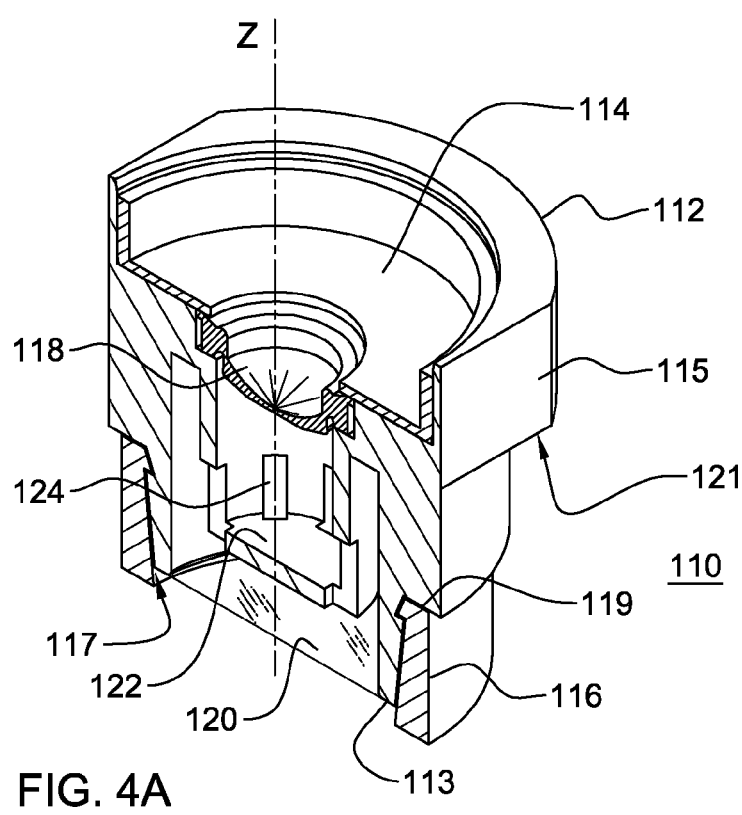

Exemplary Sample Cell:

The sample cell discussed above is disclosed in the previously filed, U.S. Patent Applications entitled PRE-FILMED PRECISION SAMPLE CELL FOR X-RAY ANALYZER, U.S. Ser. No. 60/991,396, filed on Nov. 30, 2007, and U.S. Ser. No. 12/323,590, filed on Nov. 26, 2008, each of which is incorporated by reference herein in its entirety. Summarizing, and with reference to FIGS. 4a-b (where like elements are referred to using like element numbers), a pre-filmed, precision sample cell 110 is provided. The sample cell includes an outer body 112 forming an interior sample reservoir, an upper end of which includes a fill valve 118 held in place by an exemplary friction-fitted cap 114.

The fill valve is preferably directional, i.e., 1-way to allow a sample in (via a pipette or other insertion device), but preventing a sample from leaking out. The SUREFLO or MEDIFLO directional elastomeric valves available from Liquid Molding Systems, Inc. are examples of such directional valves. Such valves can also be designed/chosen to provide an adequate venting capability of the sample reservoir in one embodiment.

The lower end of the interior sample reservoir is formed of a film 120 (e.g., mylar) which can be wrapped tightly around the lower ends 113 of the body 112, and held in place using a conformal ring. Other attachment techniques are possible, including glues, ultrasonic, RF, or other heating techniques to create a bond between the film and the body around the perimeter of the lower ends 113. The film is preferably designed with enough strength to hold the sample (and, as discussed further below, with enough strength to support the entire sample cell in the instrument), while allowing penetration of x-rays, and resultant x-ray fluorescence to/from the x-ray analysis engine. The sample can be a liquid sample, a partially-liquid sample, or a solid (e.g., powder) sample.

Film 120 may be fastened in place around the lower edge 113 of the body 112 using a conformal ring 116. In one embodiment, the ring snaps into place using barbed-shaped edges which mate with complimentary surfaces in region 119, or another snapping technique which provides an essentially permanent fit to discourage or prevent disassembly. In accordance with this aspect of the present invention, friction-fit cap 114, and/or snapping ring 116, are designed to be essentially, permanently, mounted on the body 112. This permanent mounting can be effected using friction for the cap 114, and 1-way barbs 119 for ring 116. Such permanent mounting (i.e., at a precision assembly facility) ensures that the fill valve is precisely placed, and/or the film is precisely mounted. This precise, factory-set mounting ensures precision placement, discourages tampering in the field, while allowing some level of component interchangeability, including the ability to use cut pieces of film purchased in volume, and different types of films or fill valves.

In one embodiment, an edge of the ring 116 extends beyond the lower end 113 of the body over which the film is fastened forming a recessed area 117. The sample cell can then rest upon the lower edge of ring 116, when placed on a surface, with the film being separated from the surface by a distance corresponding to the depth of the recess. This prevents contamination of the outer surface of the film 120 when the sample cell is in use.

A blocking structure 122 can also be provided within the reservoir to prevent an inserted pipette from puncturing the film 120, while allowing the sample to circulate within the reservoir. Apertures 124 in the blocking structure 122 can also be used to selectively pass certain sized particulates to the analysis area near the film.

Other features include a horizontal edge 121 which can assist/control the vertical placement of the cell in an x-ray analysis engine; and opposing faces 115 which can also be used to assist/control the horizontal/rotational placement of the cell. The precise size and film fastening of the sample cell allow for precise placement of the sample along the Z axis which, as discussed above, is critical for x-ray analysis systems.

The body and other parts discussed above can be formed using injection molding of a high density, polyethylene (HDPE) compound.

Another embodiment of a pre-filmed sample cell is disclosed in the above-incorporated U.S. patent application Ser. No. 12/323,590. Those skilled in the art will recognize that any combination of the features of the first (FIGS. 4A-B) and second (Ser. No. 12/323,590) embodiments of the sample cell can be combined without departing from the principles of the present invention.

Figure 5:
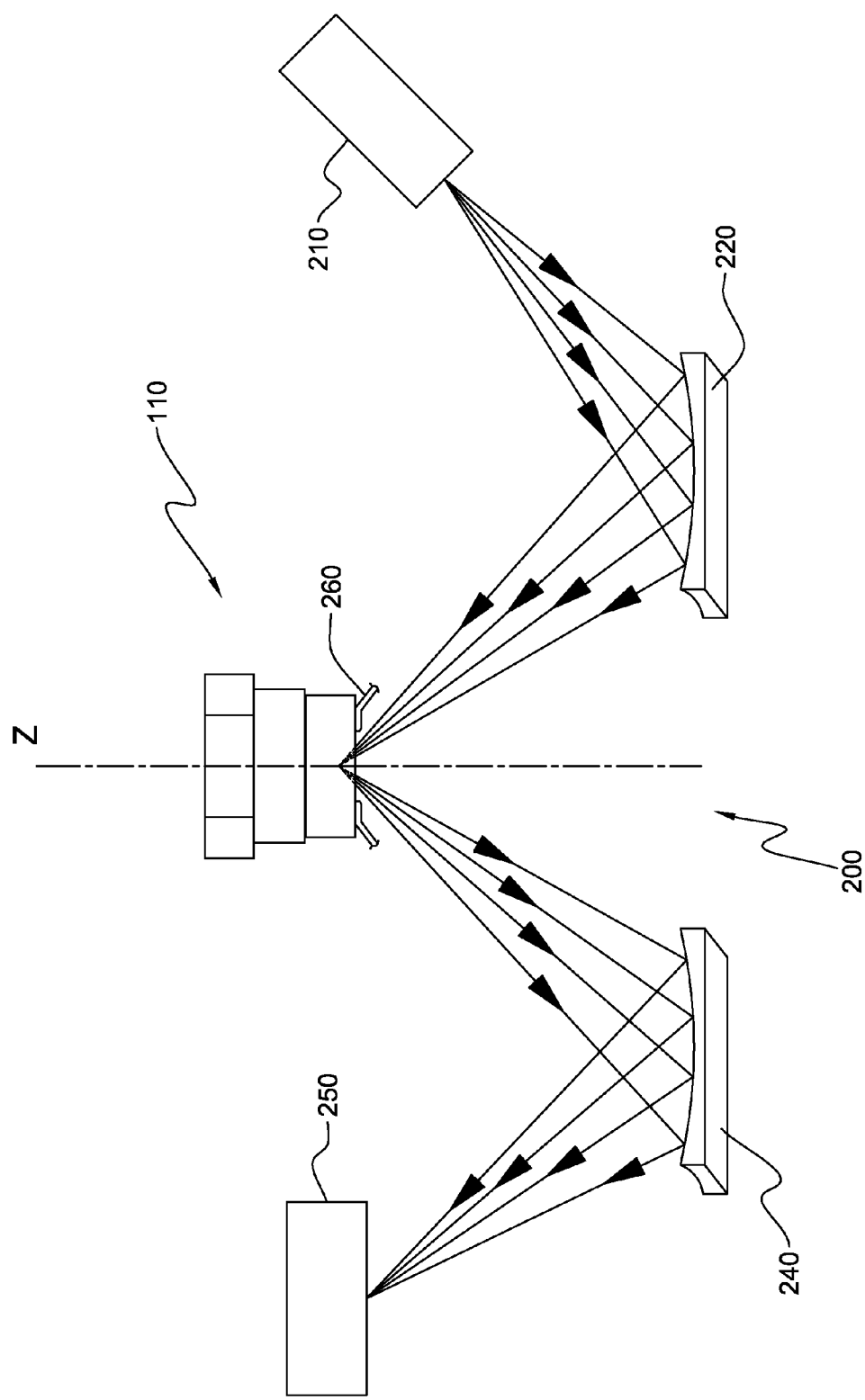
FIG. 5 is a schematic view of the sample cell aligned to a focal spot of an x-ray optic-enabled x-ray analysis engine, according to another aspect of the present invention.

Exemplary MWD XRF X-Ray Analysis System:

FIG. 5 depicts in schematic view an exemplary MWD XRF x-ray analysis engine 200 in combination with any of the above-discussed sample cells, e.g., 110, and to which the present insertion and removal apparatus may also be directed. The x-ray analysis engine has a focal spot requiring alignment with the sample in the sample cell. Engine 200 includes, in one embodiment, an x-ray source 210 and detector 250. X-ray optics 220 and/or 240 can be placed in the excitation and/or detection paths of the engine. These optics require a high degree of alignment with the sample spot to function at the requisite limits of detection discussed above. Such optics include, for example, curved crystal monochromating optics such as those disclosed in commonly assigned U.S. Pat. Nos. 6,285,506; 6,317,483; and 7,035,374; and/or multilayer optics such as those disclosed in commonly assigned U.S. patent application entitled "X-Ray Focusing Optic Having Multiple Layers With Respective Crystal Orientations," U.S. Ser. No. 11/941,377 filed Nov. 16, 2007; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is incorporated herein by reference in its entirety.

Curved monochromating optics in the excitation and detection path are shown in FIG. 5, which is the configuration of the SINDIE sulfur analyzer discussed above. However, an optic may only be present in one of these paths, which still requires precise alignment. In one example, an optic of any of the above-describe types may only be present in the excitation path, and the detection path would include an energy dispersive detector. This is the common configuration of an energy dispersive x-ray fluorescence (EDXRF) system.

In one embodiment, to ensure precision alignment of the sample to the focal spot, the sample cell could rest on one or more supports 260 which directly contact the film. The upper surfaces (not visible) of the supports are positioned in the instrument to correspond to the focal spot, and when the film surface rests on the supports, precise alignment is ensured.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A shielded sample cell insertion and removal apparatus for an x-ray analysis instrument, comprising:
    an outer body, an interior portion of which includes a sample cell setting to hold a sample cell during x-ray analysis, an outer surface of the sample cell exposing a sample to an x-ray engine; and
    a handle integrally formed within the outer body and over the sample cell setting, the handle and body formed with an x-ray absorptive material and/or plating to shield an area beyond the sample cell from x-rays transmitted from the x-ray engine;
    wherein upon moving the apparatus into and out of the instrument, the sample cell is moved into and out of an analysis position, while providing x-ray shielding beyond the sample cell from x-rays transmitted from the x-ray engine of the instrument.

2. The apparatus of claim 1, further comprising:
    a locking and release mechanism to lock the apparatus into the analyzer, and release the apparatus from the instrument.

3. The apparatus of claim 1, further comprising compression means for forcing the outer surface of the sample cell upon locking of the apparatus into the instrument.

4. An x-ray analysis instrument in combination with the apparatus of claim 1, the instrument including an aperture into and out of which the apparatus slides, and an x-ray analysis engine which transmits x-rays upwards towards the sample cell which projects from a bottom of the apparatus.

5. The combination of claim 4, further comprising:
    a triggering means to open/close an x-ray shutter based upon the position of the apparatus in the instrument.

6. The apparatus of claim 1, in combination with the sample cell.

7. The combination of claim 6, wherein the sample cell comprises:
    an outer body forming a sample reservoir therein;
    a directional fill valve disposed in an upper end of the outer body and forming an upper end of the sample reservoir, the fill valve for accepting a sample during filling, and preventing sample leakage while providing venting after filling; and
    a film covering a lower edge of the outer body, and forming a bottom end of the sample reservoir, the film for presenting the sample to an analysis focal spot of the analysis instrument.

8. An x-ray analysis engine in combination with the sample cell insertion and removal apparatus and sample cell of claim 6, the x-ray analysis engine having an x-ray focal spot requiring alignment with the sample in the sample cell insertion and removal apparatus.

9. The combination of claim 8, further comprising at least one x-ray optic disposed in an x-ray excitation and/or detection path, requiring alignment to the focal spot.

10. The combination of claim 9, wherein the at least one x-ray optic comprises a curved monochromating optic or a polycapillary optic.

11. A method for sample cell insertion and removal in an x-ray analysis instrument, comprising:
    providing an apparatus having:
        an outer body, an interior portion of which includes a sample cell setting to hold a sample cell during x-ray analysis, an outer surface of the sample cell exposing a sample to an x-ray engine; and
        a handle formed within the outer body and over the sample cell setting, the handle and body formed with an x-ray absorptive material and/or plating to shield an area beyond the sample cell from x-rays transmitted from the x-ray engine; and
    moving the apparatus into and out of the instrument, thereby moving the sample cell into and out of an analysis position, while providing x-ray shielding beyond the sample cell from x-rays transmitted from the x-ray engine of the instrument.

12. The method of claim 11, further comprising:
    locking the apparatus into the instrument, and release the apparatus from the instrument.

13. The method of claim 11, further comprising using compression means for forcing the outer surface of the sample cell upon locking of the apparatus into the instrument.

14. A method for operating an x-ray analysis instrument in combination with the method of claim 11, the instrument including an aperture into and out of which the apparatus slides, and an x-ray analysis engine which transmits x-rays upwards towards the sample cell which projects from a bottom of the apparatus.

15. The method of claim 14, further comprising:
    triggering open/close an x-ray shutter based upon the position of the apparatus in the instrument.

* * * * *